US00PP27387P3

(12) United States Plant Patent
Braeunig

(10) Patent No.: US PP27,387 P3
(45) Date of Patent: Nov. 15, 2016

(54) ***EUPHORBIA* PLANT NAMED 'FLOREUPRED'**

(50) Latin Name: ***Euphorbia* hybrid**
Varietal Denomination: Floreupred

(71) Applicant: Florensis B.V., Hendrik-Ido-Ambacht (NL)

(72) Inventor: Tobias Braeunig, Quedlinburg (DE)

(73) Assignee: Florensis B.V., Hendrik-Ido-Ambacht (NL)

( * ) Notice: Subject to any disclaimer, the term of this patent is extended or adjusted under 35 U.S.C. 154(b) by 48 days.

(21) Appl. No.: 14/545,586

(22) Filed: May 26, 2015

(65) Prior Publication Data

US 2015/0366120 P1 Dec. 17, 2015

Related U.S. Application Data

(60) Provisional application No. 61/998,032, filed on Jun. 16, 2014.

(51) Int. Cl.
*A01H 5/02* (2006.01)

(52) U.S. Cl.
USPC ..... Plt./302

(58) Field of Classification Search
USPC ..... Plt./302
See application file for complete search history.

*Primary Examiner* — Keith Robinson
(74) *Attorney, Agent, or Firm* — Audrey Charles

(57) ABSTRACT

A new and distinct cultivar of *Euphorbia* plant named 'Floreupred', characterized by its dark green-colored foliage that turns dark burgundy with increased sun exposure, moderate growth vigor, and well-branched, compact growth habit, is disclosed.

1 Drawing Sheet

Latin name of genus and species of plant claimed: *Euphorbia* hybrid.

Variety denomination: 'Floreupred'.

BACKGROUND OF THE INVENTION

The present invention relates to a new and distinct cultivar of *Euphorbia* plant botanically known as *Euphorbia* hybrid and hereinafter referred to by the cultivar name 'Floreupred'.

The new cultivar originated in a controlled breeding program in Quedlinburg, Germany during June 2008. The objective of the breeding program was the development of dark-leaved, more compact, and well-branched *Euphorbia*.

The new *Euphorbia* cultivar is the result of open-pollination within an insect-cage environment. The female (seed) parent of the new cultivar is a *Euphorbia amygdaloides* selection coded 3810-5, not patented, characterized by its light green-colored foliage, and vigorous, upright growth habit. The male (pollen) parent of the new cultivar is an unknown *Euphorbia,* not patented. Species plants included in the cage environment include but are not limited to *E. baselicis, E. cyparissias, E. amygdaloides, E. myrsinites, E. dulcis, E. nicaeensis, E. walichii,* and *E. hypericifolia.* The new cultivar was discovered and selected as a single flowering plant within the progeny of the above stated open-pollination during May 2009 in a controlled environment in Quedlinburg, Germany.

Asexual reproduction of the new cultivar by terminal stem cuttings since May 2009 in Quedlinburg, Germany and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Floreupred' as a new and distinct cultivar of *Euphorbia* plant:

1. Dark green-colored foliage that turns dark burgundy with increased sun exposure;
2. Moderate growth vigor; and
3. Well-branched, compact growth habit.

Plants of the new cultivar differ from plants of the female parent primarily in foliage color and in having a more compact growth habit.

Of the many commercially available *Euphorbia* cultivars, the most similar in comparison to the new cultivar is Ruby Glow 'Waleuphglo', U.S. Plant Pat. No. 22,200. However, in comparison, plants of the new cultivar differ from plants of 'Waleuphglo' in at least the following characteristics:

1. Plants of the new cultivar have leaves in alternate arrangement unlike plants of 'Waleuphglo';
2. Plants of the new cultivar have a longer internode length than plants of 'Waleuphglo';
3. Plants of the new cultivar have ovate-shaped cyathophylls unlike plants of 'Waleuphglo'; and
4. Plants of the new cultivar has a foliage color different from plants of 'Waleuphglo'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Floreupred'. The plants were grown in one-gallon containers for 30 weeks in a greenhouse in Elburn, Ill. Plants were pinched once prior to transplant in the gallon containers. Approximately 4 weeks after transplant, plants were cut to 8 inches above the soil level.

DETAILED BOTANICAL DESCRIPTION

Figure 1:
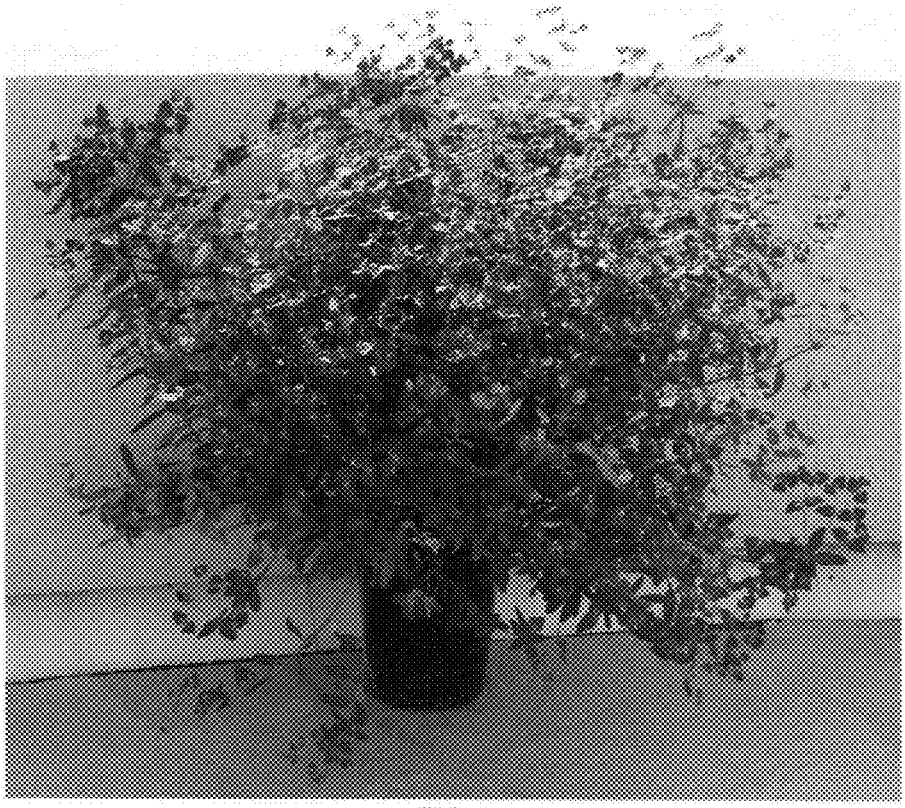
FIG. 1 illustrates a side view of the overall growth of 'Floreupred'.
Figure 2:
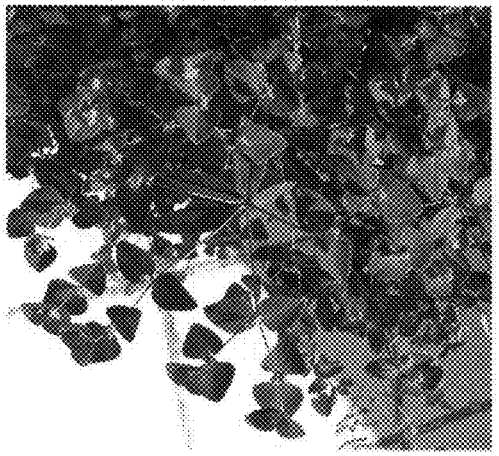
FIG. 2 illustrates a close-up view of the inflorescences of 'Floreupred'.
Figure 3:
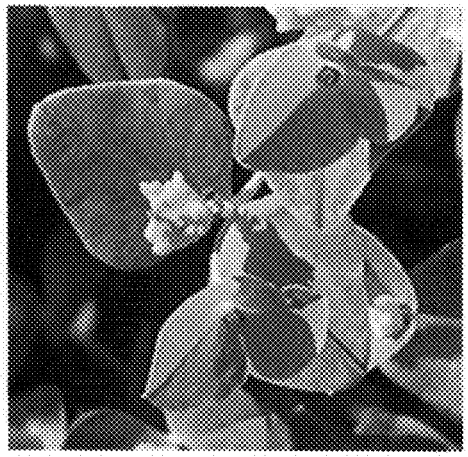
FIG. 3 illustrates a close-up view of an individual cyathium of 'Floreupred'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in May 2015 under natural light conditions in West Chicago, Ill.

The following descriptions and measurements describe plants produced from cuttings from stock plants and grown in a glass-covered greenhouse in Elburn, Ill. The plants were grown for 30 weeks in one-gallon containers utilizing a soilless growth medium and were pinched once prior to transplant. Approximately 4 weeks after transplant, plants were cut to 8 inches above the soil level. Greenhouse temperatures were maintained at approximately 45° F. to 55° F. (7° C. to 13° C.) during the day and approximately 35° F. to 45° F. (2° C. to 7° C.) during the night. No supplemental lighting was used. Measurements and numerical values represent averages of typical plants.

Botanical classification: *Euphorbia* hybrid cultivar Floreupred.

Parentage:

*Female parent.*—A *Euphorbia amygdaloides* selection coded 3810-5, not patented.

*Male parent.*—Unknown *Euphorbia*, not patented.

Propagation:

*Type cutting.*—Terminal stem.

*Time to initiate roots.*—Approximately 15 to 18 days.

*Time to produce a rooted cutting.*—Approximately 5 to 6 weeks.

*Root description.*—Fine, fibrous.

*Rooting habit.*—Freely branching.

Plant description:

*Commercial crop time.*—Approximately 10 to 12 weeks from a rooted cutting to finish in a one-gallon container.

*Growth habit and general appearance.*—Moderately vigorous, compact.

*Size.*—Height from soil level to top of plant plane: Approximately 58.0 cm. Width: Approximately 70.0 cm.

*Branching habit.*—Freely branching, divergent, pinching enhances branching. Quantity of branches per plant: Approximately 100.

*Branch.*—Shape: Round in cross section. Strength: Strong, flexible. Length to base of inflorescence: Approximately 48.0 cm. Diameter: Approximately 4.0 mm. Length of central internode: Approximately 3.0 cm. Texture: Sparsely pubescent. Color of young stems: 146D. Color of mature stems: 146D with a heavy overlay of 187A, overlay darkens with sun exposure.

Foliage description:

*General description.*—Quantity of leaves per branch: Approximately 20, with a whorl of 5 leaves at base of terminal inflorescence. Fragrance: None detected. Form: Simple. Arrangement: Alternate.

*Leaves* (*stem*).—Aspect: Primarily perpendicular to stem. Shape: Oblong. Margin: Entire. Apex: Broadly acute. Base: Rounded. Venation pattern: Pinnate. Length of mature leaf: Approximately 6.0 cm. Width of mature leaf: Approximately 1.8 cm. Texture of upper surface: Glabrous. Texture of lower surface: Moderately pubescent. Color of upper surface of young foliage: 137A with venation of 145C. Color of lower surface of young foliage: Closest to 191A, venation indistinguishable from lamina or faintly colored 187D, midvein of 145D with a faint overlay of 187D. Color of upper surface of mature foliage: N137A with an overlay of 187A, overlay darkens with sun exposure, venation indistinguishable from lamina, midvein of 187B. Color of lower surface of mature foliage: 191A with an overlay of 187B, venation indistinguishable from lamina or faintly colored 187B, midvein of 187C.

*Leaves* (*at inflorescence base*).—Aspect: Primarily perpendicular to stem, in a whorl of 5 leaves. Shape: Ovate. Margin: Entire. Apex: Broadly acute. Base: Rounded, sessile. Venation pattern: Pinnate. Length of mature leaf: Approximately 3.3 cm. Width of mature leaf: Approximately 1.3 cm. Texture of upper surface: Glabrous. Texture of lower surface: Moderately pubescent. Color of upper surface of young foliage: 137A with venation of 145C. Color of lower surface of young foliage: Closest to 191A, venation indistinguishable from lamina or faintly colored 187D, midvein of 145D with a faint overlay of 187D. Color of upper surface of mature foliage: N137A with an overlay of 187A, overlay darkens with sun exposure, venation indistinguishable from lamina, midvein of 187B. Color of lower surface of mature foliage: 191A with an overlay of 187B, venation indistinguishable from lamina or faintly colored 187B, midvein of 187C.

*Petiole* (*on stem leaves only*).—Length: Approximately 2.0 mm. Diameter: Approximately 2.0 mm. Texture: Moderately pubescent. Color: 146C tinted with 187A when mature.

Flowering description:

*Flowering habit.*—Inflorescences of 'Floreupred' are ornamentally insignificant. After exposure to short days 'Floreupred' blooms under outdoor growing conditions from early to late spring.

*Lastingness of individual cyanthium.*—Approximately 20 to 30 days.

Inflorescence description:

*General description.*—Type: Cyathia arranged in terminal and axillary cymes, terminal cymes having 5 axes. Aspect: Facing upward and outward. Quantity of inflorescences per plant: Approximately 80 terminal cymes and up to 7 axillary cymes per branch.

Fragrance: None detected. Depth or height of cyme: Approximately 8.0 cm. Width: Approximately 4.3 cm.

*Rachis.*—Strength: Strong. Aspect: Acute angle to stem. Length: Approximately 5.5 cm. Diameter: Approximately 1.0 mm. Texture: Glabrous. Color: 146C maturing to 187A.

Flower description:

*Bud just before opening.*—Shape: Oblong. Length: Approximately 2.0 mm. Diameter: Approximately 1.0 mm. Texture: Glabrous. Color: 145D.

*Cyathia.*—Quantity per rachis: 3. Appearance: One pistil and two stamens; stamens located within a tubular involucre that surrounds the pedicel (pistil stalk); involucre has 4 petaloid nectaries at the upper rim, one pair of cyathophylls at base of involucre. Fragrance: Not detected. Depth: Approximately 9.0 mm. Width: Approximately 3.0 cm.

*Involucre.*—Length: Approximately 4.0 mm. Width: Approximately 2.0 mm. Texture of upper and lower surfaces: Glabrous. Color: Lighter than 145D, quickly senesces to 199D. Length of petaloid nectaries: Approximately 1.0 mm. Width of petaloid nectaries: Approximately 1.0 mm. Texture of upper and lower surfaces: Glabrous. Color: 183A, quickly senesces to 202A.

*Cyathophylls.*—Quantity: 2 per cyathium. Arrangement: Opposite. Shape: Ovate. Margin: Entire. Apex: Broadly acute. Base: Rounded, sessile. Length: Approximately 1.9 cm. Width: Approximately 1.4 cm. Texture of upper and lower surfaces: Glabrous. Color of upper surface of young cyathophylls: 137A with venation of 137C. Color of lower surface of young cyathophylls: Closest to 191A, venation indistinguishable from lamina or faintly colored 187D, midvein of 145D. Color of upper surface of mature cyathophylls: N137A with an overlay of 187A, overlay darkens with sun exposure, venation indistinguishable from lamina, midvein of 187B at base of cyathophylls. Color of lower surface of mature cyathophylls: 191A with an overlay of 187B, venation indistinguishable from lamina or faintly colored 187B.

*Pedicel.*—Length: Approximately 4.0 mm. Diameter: Approximately 1.0 mm. Texture: Glabrous. Color: 144C.

*Reproductive organs.*—Androecium: Stamen quantity: 2. Length: Approximately 1.0 mm. Anther shape: Oval. Anther color: 154D, quickly senesces. Pollen amount: None observed. Gynoecium: Pistil quantity: 1 per cyathium, ovary supported on a pedicel, 3 styles each 2-cleft, 6 stigmas. Pistil length (not including pedicel): Approximately 5.0 mm. Stigma shape: Rounded. Stigma width: Less than 1.0 mm. Stigma color: 183A. Style length: Approximately 2.0 mm. Style color: 137A. Ovary length: Approximately 3.0 mm. Ovary diameter: Approximately 5.0 mm. Ovary texture: Verrucose. Ovary color: 137A at style transitioning through 144A to 144C at pedicel end, dotted with 187C.

Seed and fruit production: Neither seed nor fruit production has been observed.

Disease and pest resistance: Resistance to pathogens and pests common to *Euphorbia* has not been observed.

What is claimed is:

1. A new and distinct cultivar of *Euphorbia* plant named 'Floreupred', substantially as herein illustrated and described.

* * * * *